United States Patent
Hill et al.

(10) Patent No.: US 11,246,858 B2
(45) Date of Patent: Feb. 15, 2022

(54) IMMUNORESPONSIVE METHODS OF TREATING TUMORS

(71) Applicant: Institut Pasteur de Montevideo, Montevideo (UY)

(72) Inventors: Marcelo Hill, Canelones (UY); Mercedes Segovia, Canelones (UY); Sofia Russo, Canelones (UY); Mathias Jeldres, Montevideo (UY); Maria Romina Girotti, Buenos Aires (AR); Maite Duhalde Vega, Buenos Aires (AR); Yamil Damián Mahmoud, Buenos Aires (AR)

(73) Assignee: INSTITUT PASTEUR DE MONTEVIDEO, Montevideo (UY)

(*) Notice: Subject to any disclaimer, the term of this patent is extended or adjusted under 35 U.S.C. 154(b) by 0 days.

(21) Appl. No.: 15/969,350

(22) Filed: May 2, 2018

(65) Prior Publication Data
US 2018/0318273 A1 Nov. 8, 2018

Related U.S. Application Data

(60) Provisional application No. 62/500,113, filed on May 2, 2017.

(51) Int. Cl.
*A61K 31/4422* (2006.01)
*A61P 35/00* (2006.01)
*A61K 39/395* (2006.01)
*C07K 16/28* (2006.01)

(52) U.S. Cl.
CPC ...... *A61K 31/4422* (2013.01); *A61K 39/3955* (2013.01); *A61P 35/00* (2018.01); *C07K 16/2818* (2013.01); *C07K 16/2827* (2013.01)

(58) Field of Classification Search
CPC . A61K 31/4422; A61K 39/3955; A61P 35/00; C07K 16/2818; C07K 16/2827
See application file for complete search history.

(56) References Cited

FOREIGN PATENT DOCUMENTS

JP          2012-100629 A    5/2012
WO         2015/059463 A2    4/2015

OTHER PUBLICATIONS

Goto (Year: 1996).*
Hoang (Year: 1997).*
Young (Year: 1988).*
Louvet (Year: 2005).*
Cuajungco (Year: 2012).*
Yakimchuk et al (Year: 2011).*
Hu et al (Year: 2007).*
Wang et al (Year: 2004).*
Teixeira et al (Year: 2005).*
Wang et al (Year: 2016).*
Gao et al (Year: 2016).*
Zawadzki (Year: 2008).*
International Search Report for International Application No. PCT/IB18/053059 dated Jul. 2, 2018, European Patent Office, Netherlands.
Written Opinion of the International Searching Authority for International Application No. PCT/IB18/053059 dated Jul. 2, 2018, European Patent Office, Netherlands.
Franckowiak et al., "The Optical Isomers of the 1,4-Dihydropyridine Bay K 8644 Show Opposite Effects on Ca Channels," European Journal of Pharmacology 114: 223-226 (1985).

* cited by examiner

*Primary Examiner* — Jeffrey S Lundgren
*Assistant Examiner* — Ibrahim D Bori
(74) *Attorney, Agent, or Firm* — Cozen O'Connor

(57) ABSTRACT

Within the scope of the present invention is a new pharmacological strategy for the treatment of tumors based on anti-tumoral immune responses.

15 Claims, 25 Drawing Sheets

IMMUNORESPONSIVE METHODS OF TREATING TUMORS

BACKGROUND

Manipulation of the immune system to trigger anti-tumoral immune responses has revolutionized the therapeutic approach of a variety of cancers ([1], [2], and [3]). An immune checkpoint blockade unleashes naturally occurring T cells that are able to recognize cancer cells, by eliminating negative signals that normally hold those T cells in check to prevent autoimmune attack. Presently, two immunotherapeutic strategies are currently being used in the clinic. One targets cytotoxic T lymphocyte-associated protein (CTLA)-4 [4]. The other targets the programmed cell death 1 (PD-1)/PD ligand 1 (PD-L1) pathway [4]. However, only a minority of patients treated with these drugs experience substantial clinical benefit.

SUMMARY

The present invention described herein fulfills an unmet need for new pharmacological strategies to treat tumors via anti-tumoral immune responses. In one embodiment, this pharmacological approach manipulates expression of the Tmem176b gene, also known as TORID (TOlerance Related and InduceD), to treat tumors. TORID is highly expressed by macrophages and dendritic cells (DCs) ([5] and [6]). Prior studies demonstrated that expressed TORID promotes antigen presentation to CD8+ T cells via the cross-presentation pathway [7]. Thus, TORID deficiency would have been expected to lead to decreased immune responses mediated by CD8+ Tcells.

However, contrary to current thinking the inventors herein discovered that TORID knock-out mice increased CD8+ T cell-mediated anti-tumor activity. While not wishing to be bound by any theory, the inventors herein have presented evidence that TORID may not promote effector CD8+ T cells. The inventors' investigation also supports that anti-tumoral CD8+ T cells can be generated in vivo through antigen presentation pathways different from cross-presentation such as direct presentation by tumor cells.

Thus one embodiment of the present invention is a method of inhibiting TORID to impair tumor growth that includes exposing TORID to a pharmacologically active amount of an ion channel modulator. In one embodiment, the ion channel modulator is a molecule for which different isomers can act as activator or inhibitor of voltage-gated calcium channels. In another embodiment, the calcium channel agonist is BAY K8644. In another embodiment, both isomers [(−) and (+)] inhibit TORID-dependent ion fluxes.

Another embodiment is a method of treating a tumor that includes administering a therapeutically effective amount of an ion channel modulator to a patient in need thereof. In one embodiment, the ion channel modulator is a calcium channel agonist. In another embodiment, the calcium channel agonist is BAY K8644. In another embodiment, the method of treating the tumor includes administering one or more second therapeutic agents to a patient in need thereof. In one embodiment, the second therapeutic agent is administered concurrently with the ion channel ligand. In one embodiment, the second therapeutic agent is administered sequentially with the ion channel ligand. In one embodiment, the second therapeutic agent is an anti-CTLA4 antibody or an anti-PD-1/PD-L1 antibody. In one embodiment, the second therapeutic agent is radiation therapy. In one embodiment, the second therapeutic agent is an anti-CTLA4 antibody or an anti-PD-1/PD-L1 antibody and radiation therapy.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

DETAILED DESCRIPTION

Figure 1:
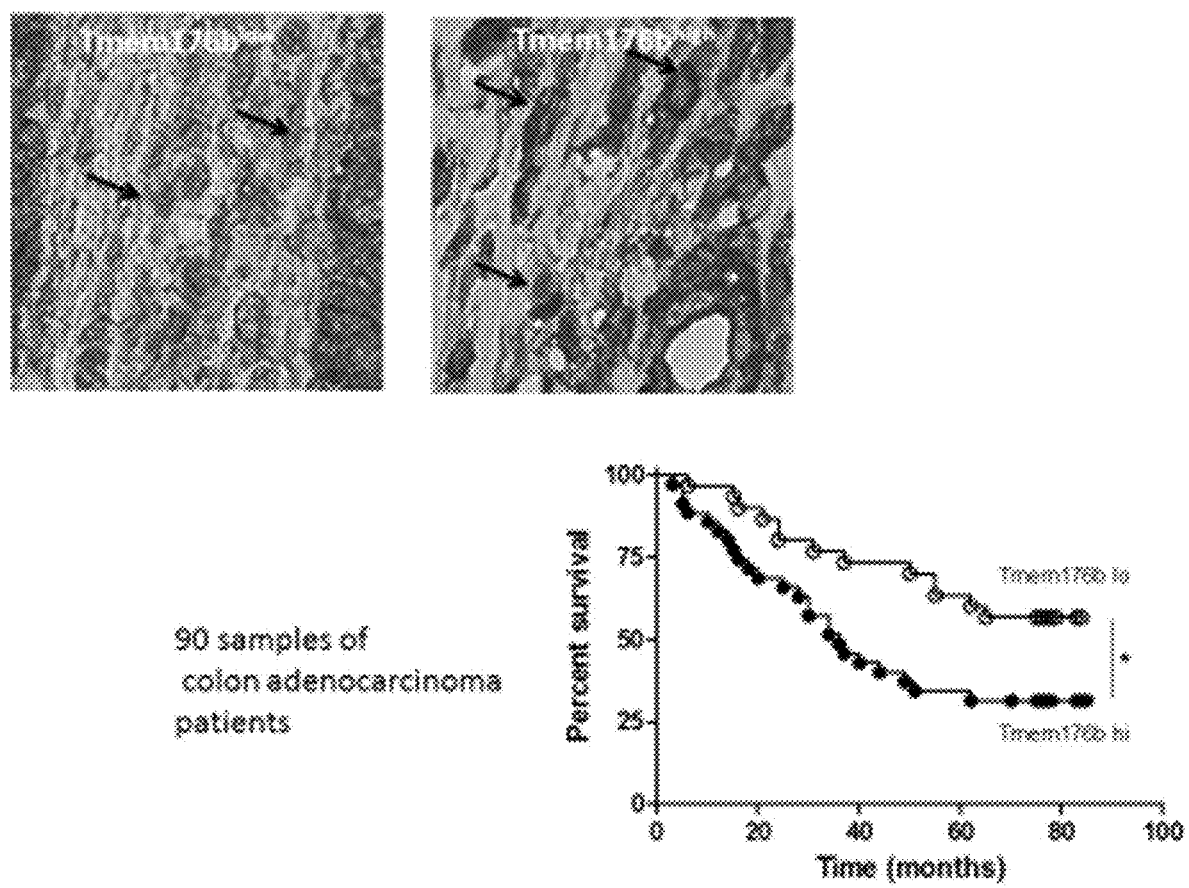
FIG. 1 demonstrates that stromal TORID is associated with diminished survival in human colon cancer.

Before the present methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a," "an," and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 5% of the numerical value of the number with which it is being used. Therefore, about 50% means in the range of 45%-55%.

"Composition" as used herein is intended to encompass a product comprising the specified ingredients in the specified amounts, as well as any product which results, directly or indirectly, from combination of the specified ingredients in the specified amounts. Such term in relation to "pharmaceutical composition" is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound to the present invention and a pharmaceutically acceptable carrier. A composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment.

"Administering" when used in conjunction with a therapeutic means to administer a therapeutic directly to a subject, whereby the agent positively impacts the target. "Administering" a composition or compound may be accomplished by, for example, injection, oral administration, topical administration, or by these methods in combination with other known techniques. Such combination techniques include heating, radiation, ultrasound and the use of delivery agents. When a compound is provided in combination with one or more other active agents (e.g. other anti-atherosclerotic agents such as the class of statins), "administration" and its variants are each understood to include concurrent and sequential provision of the compound or salt and other agents.

As used herein, the term "agent," "active agent," "therapeutic agent," or "therapeutic" means a compound or composition utilized to treat, combat, ameliorate, prevent or improve an unwanted condition or disease of a patient. Furthermore, the term "agent," "active agent," "therapeutic agent," or "therapeutic" encompasses a combination of one or more of the compounds of the present invention. One preferred therapeutic agent is BAY K8644 (Methyl 2,6-dimethyl-5-nitro-4-[2-(trifluoromethyl)phenyl]-1,4-dihydropyridine-3-carboxylate).

A "pharmacologically active amount" of a compound as used herein is a predetermined amount calculated to achieve a response from a biochemical pathway subjected to the compound. The response may be evidenced by spectroscopic measurement, isotopic labeling, or any other method conventionally used to investigate biochemical mechanisms.

A "therapeutically effective amount" or "effective amount" of a therapeutic is a predetermined amount calculated to achieve the desired effect, i.e., to inhibit, block, or reverse the activation, migration, proliferation, alteration of cellular function, and to preserve the normal function of cells. The activity contemplated by the methods described herein includes both medical therapeutic and/or prophylactic treatment, as appropriate, and the therapeutics of the invention may be used to provide improvement in any of the conditions described. It is also contemplated that the therapeutics described herein may be administered to healthy subjects or individuals not exhibiting symptoms but who may be at risk of developing a particular disorder. The specific dose of a therapeutic agent administered according to this invention to obtain therapeutic and/or prophylactic effects will, of course, be determined by the particular circumstances surrounding the case, including, for example, the therapeutic agent administered, the route of administration, and the condition being treated. However, it will be understood that the chosen dosage ranges are not intended to limit the scope of the invention in any way. A therapeutically effective amount of a therapeutic of this invention is typically an amount such that when it is administered in a physiologically tolerable excipient composition, it is sufficient to achieve an effective systemic concentration or local concentration in the tissue.

The terms "treat," "treated," "treating," and "treatment" as used herein refer to both therapeutic and prophylactic or preventative measures, wherein the object is to prevent or slow down (lessen) an undesired physiological condition, disorder, or disease, or to obtain beneficial or desired clinical results in a person or animal.

The inventors of the present invention discovered that genetic deletion and pharmacologic inhibition of TORID is associated with anti-tumoral immune responses. To manipulate TORID, the inventors took advantage of ionic disbalances within the tumor microenvironment that lead to T cell dysfunction by inhibiting $Ca^{++}$-dependent $K^+$ channels expressed in anti-tumoral T lymphocytes. TORID is a cation channel with immunoregulatory properties.

Two different tumor cell lines showed impaired growth in TORID knock out (KO) mice. Tumors from TORID KO mice showed a significantly increased infiltration by total and tumor-specific $CD8^+$ T cells. In vivo cytotoxicity experiments showed that tumor bearing TORID KO mice had an increased $CD8^+$ T cell-dependent cytotoxic capacity as compared to wild type (WT) animals. In the tumor-draining lymph node, TORID mice showed increased caspase −1 activation (FACS and western blot studies) and Th-17 cells as compared to WT animals. In TORID KO mice, tumors were rejected in a $CD8^+$ T cell, IL-1β and IL-17-dependent manner. In vivo TORID deficiency was associated with increased caspase 1 activation in $CD11b^+$ dendritic cells. In vitro, increased inflammasome activation in TORID bone marrow dendritic cells (BMDCs) was dependent on cytosolic $Ca^{++}$ and $K^+$ efflux and may involve $Ca^+$-dependent channels. High-throughput screening identified the drug (TORID Inhibitor) TI as an inhibitor of TORID-dependent $Na^+$ influx. In vivo treatment with TI led to impaired tumor growth. TI treatment in WT animals phenocopied tumor rejection observed in untreated TORID KO mice since it depended on caspase 1. In human colon tumors, high stromal Tmem176b (TORID) expression was significantly associated to poor survival. Preferably, the TI is BAY K8644. One embodiment of the present invention includes pharmacological inhibition TORID for tumor treatment.

Biologic Activity

The following methods described are used in order to demonstrate biological activity and therapeutic use, and should not be construed in any way as limiting the scope of the invention.

FIG. 1 demonstrates that stromal TORID is associated with diminished survival in human colon cancer. The study included 90 samples of human colon adenocarcinoma studied for TORID expression by immunohistochemistry. The arrows point to staining that indicate stromal cells positive for TORID in tissues counter-stained with hematoxylin. The samples were classified by the extent of stromal TORID expression. Samples with stromal TORID expression as shown in the upper-left, were classified as "low." Samples with stromal TORID expression as shown in the upper-right, were classified as "high." The study was done by two independent operators in a blind fashion. That is, low and high classification were done without knowing the survival time for the patient from which he sample was obtained. Analysis of the survival time for each case showed that "high" expression of stromal TORID was significantly associated with diminished survival time as mapped by a Log-Rank (Mantel-Cox) Test, p=0.0194.

Figure 2:
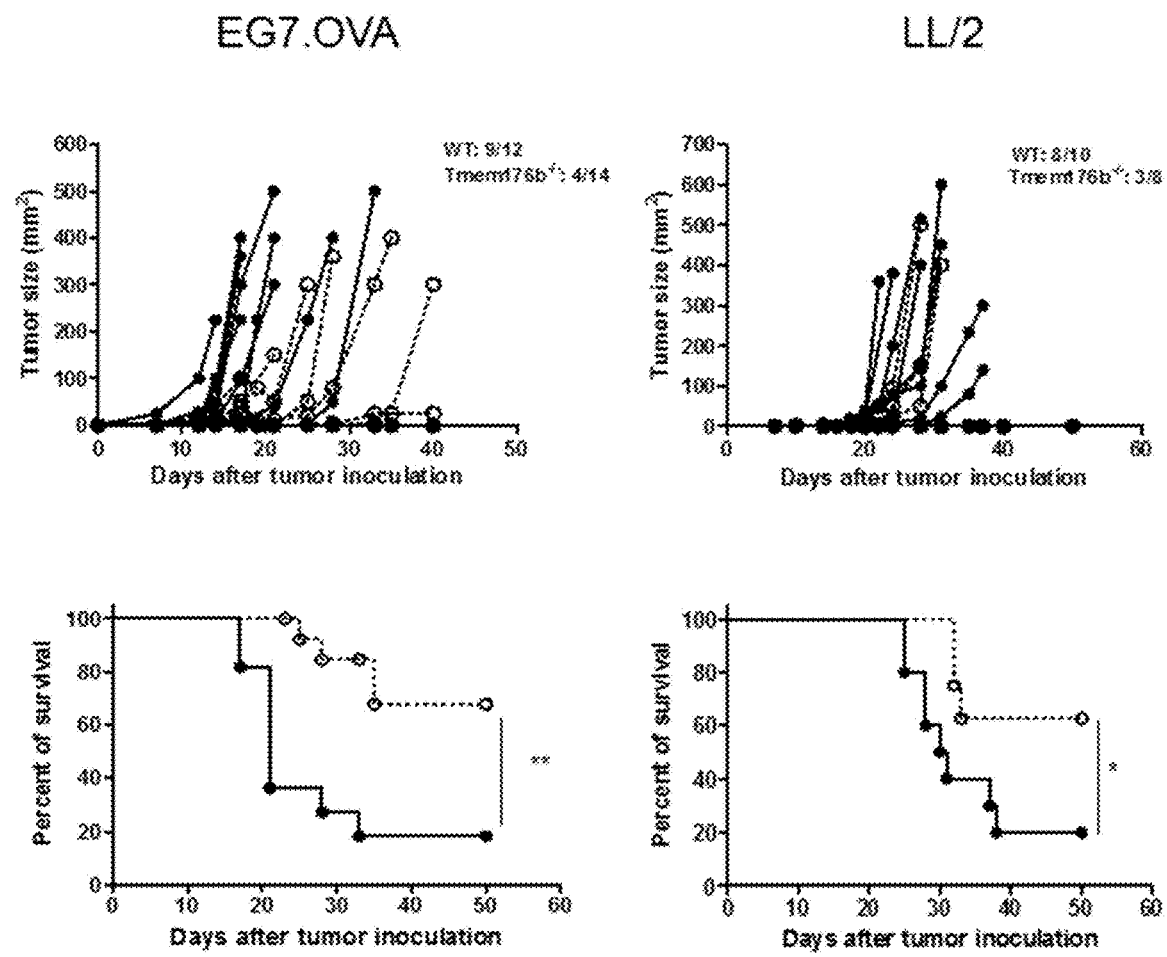
FIG. 2 demonstrates that impairing TORID expression impaired tumor growth and increased survival rate.

FIG. 2 demonstrates that impairing TORID expression impaired tumor growth and increased survival rate. The study used wild type or TORID knock-out ("KO" or "−/−") mice with lung cancer (LL/2) or thymic lymphoma (EG7.OVA). The mice were injected subcutaneously ("s/c"), and tumor size was measured every three days. The data was mapped using the Log-Rank (Mantel-Cox) Test. As shown, tumor size in the TORID KO mice was smaller in subsequent days after inoculation with tumor cells. Further, the rate of survival in TORID KO mice was substantially higher.

Figure 3:
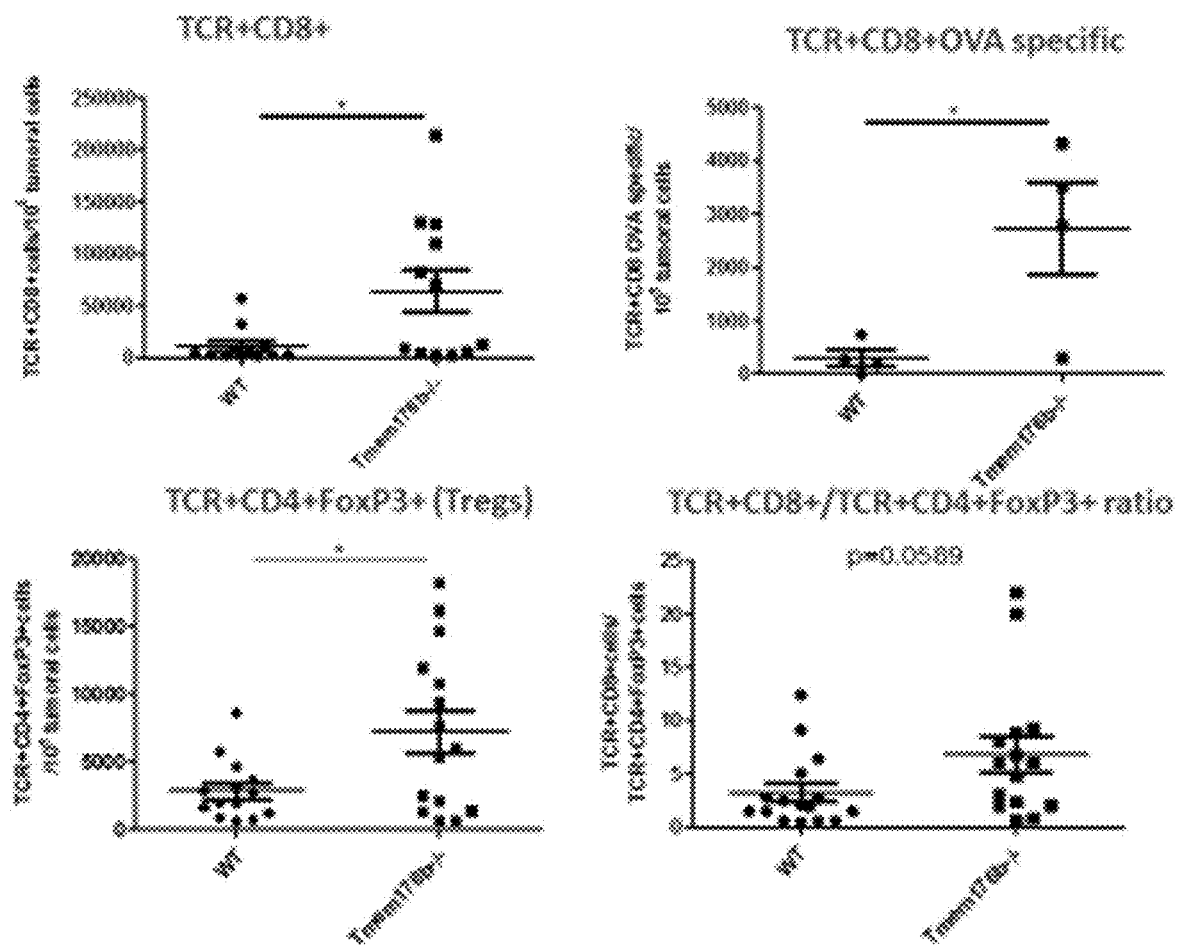
FIG. 3 shows an increased amount of anti-tumoral CD8+ T cells in TORID knock-out (KO) mice as compared to wild type mice.
Figure 4:
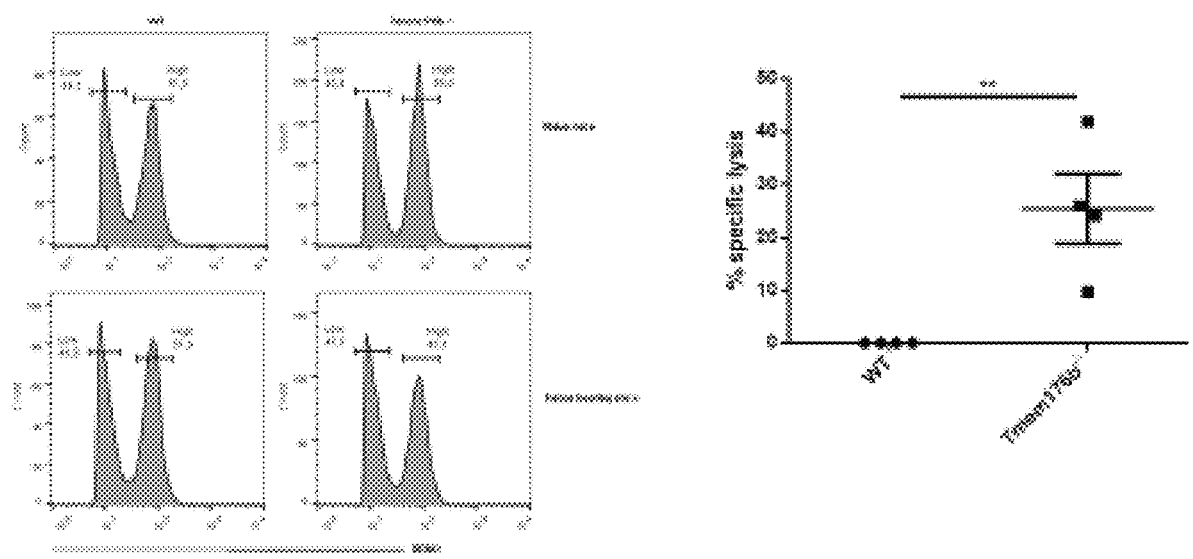
FIG. 4 shows increased in vivo CD8+ T cell-mediated cytotoxicity against tumoral antigens in TORID KO mice.
Figure 5:
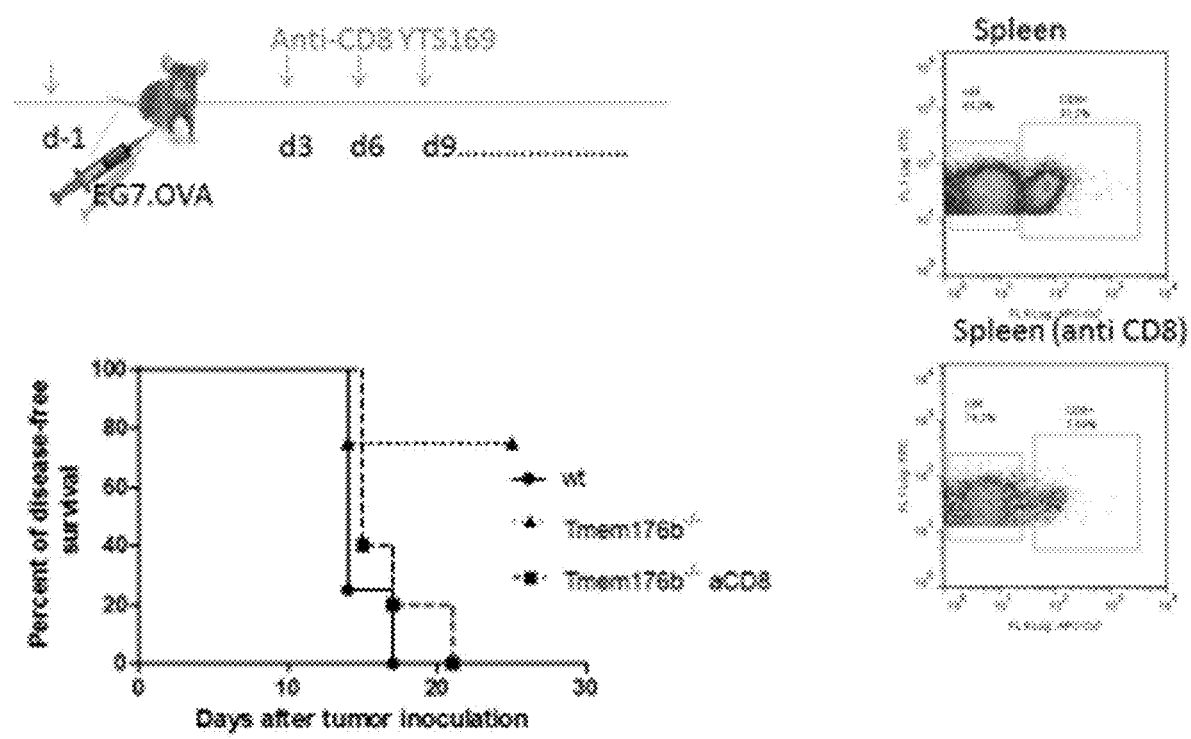
FIG. 5 shows in vivo data indicating that tumor rejection in TORID KO mice is mediated by CD8+ T cells.

Data in FIGS. 3 through 5 indicate that the tumor rejection exhibited in TORID KO mice as shown in FIG. 2 is mediated by anti-tumoral CD8+ T cells. As shown in FIG. 3, increased anti-tumoral CD8+ T cells in TORID knock-out (KO) mice compared to wild type mice. The level of CD8+ T cells increased despite higher levels of TCR, CD4, FoxP3, and T regulatory cells. This is unexpected in view of prior studies, which indicated that TCR, CD4, FoxP3, and T regulatory cells suppress antitumor effector cells such as CD8+ T cells, natural killer (NK) cells, natural killer T (NKT) cells, and helper T cells (Th) [8]. FIG. 3 illustrates data from mice injected with EG7.OVA tumor cells. Twelve days after injection, the tumor was harvested and treated with collagenase. The cell suspension was stained with antibodies and analyzed by fluorescence-activated cell sorting ("FACS"). Malignant cells were identified through staining with anti-TCR Vβ12 antibody. Within TCR Vβ12 cells, the depected cell populations were quantified. OVA specific CD8+ T cells were identified using H-2Kb (SIINFEKL) pentamers.

FIG. 4 shows that increased in vivo CD8+ T cell-mediated cytotoxicity is specific against tumoral antigens in TORID KO mice. The study was performed by intravenously injecting wild-type and KO EG7.OVA tumor-bearing mice (10 days after tumor inoculation) with splenocytes from naive C57Bl/6 mice loaded with class I OVA peptide SIINFEKL. The splenocytes were stained with high doses of [7-hydroxy-9H-(1,3-dichloro-9,9-dimethylacridin-2-one)] ("DDAO"), CAS No. 118290-05-4. An equal number of splenocytes not loaded with OVA peptide and stained with low DDAO was injected at the same time. Four hours later, the splenocytes were analyzed by FACS to quantify the injected low and high DDAO populations. The percentage of specific lysis was calculated using the following formula:

$$\% \text{ Specific Lysis} = 1 - \left[\frac{r \text{ naive}}{r \text{ with tumor}}\right] * 100$$

In the equation above, $$r = \frac{\% \, DDAO \text{ low cells}}{\% \, DDAO \text{ high cells}}.$$

The in vivo data shown in FIG. 5 demonstrates that tumor rejection in TORID KO mice is mediated by CD8+ T cells. In this study, CD8+ T cells were depleted in vivo in tumor-bearing mice via four injections of anti-CD8 antibodies (clone YTS163) on day 1, day 3, day 6, and day 9. The dot plots to the right show, by flow cytometry, a comparison between CD8+ T cells of a positive control mouse spleen (top) and depletion of CD8+ T cells of a mouse spleen after exposure to the anti-CD8 antibodies (bottom). Disease-free survival analysis showed that TORID KO mice with depleted CD8+ T cells exhibited a similar reduction in survival as compare to wild type tumor-bearing mice. In contrast, TORID KO mice with CD8+ T cells showed a higher rate of disease-free survival.

Figure 6:
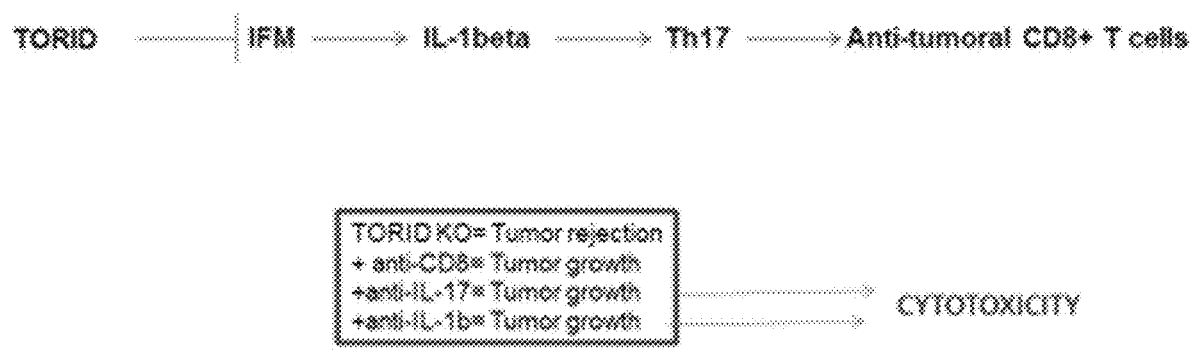
FIG. 6 illustrates a mechanism of regulating anti-tumoral CD8+ T cells via TORID manipulation.
Figure 7:
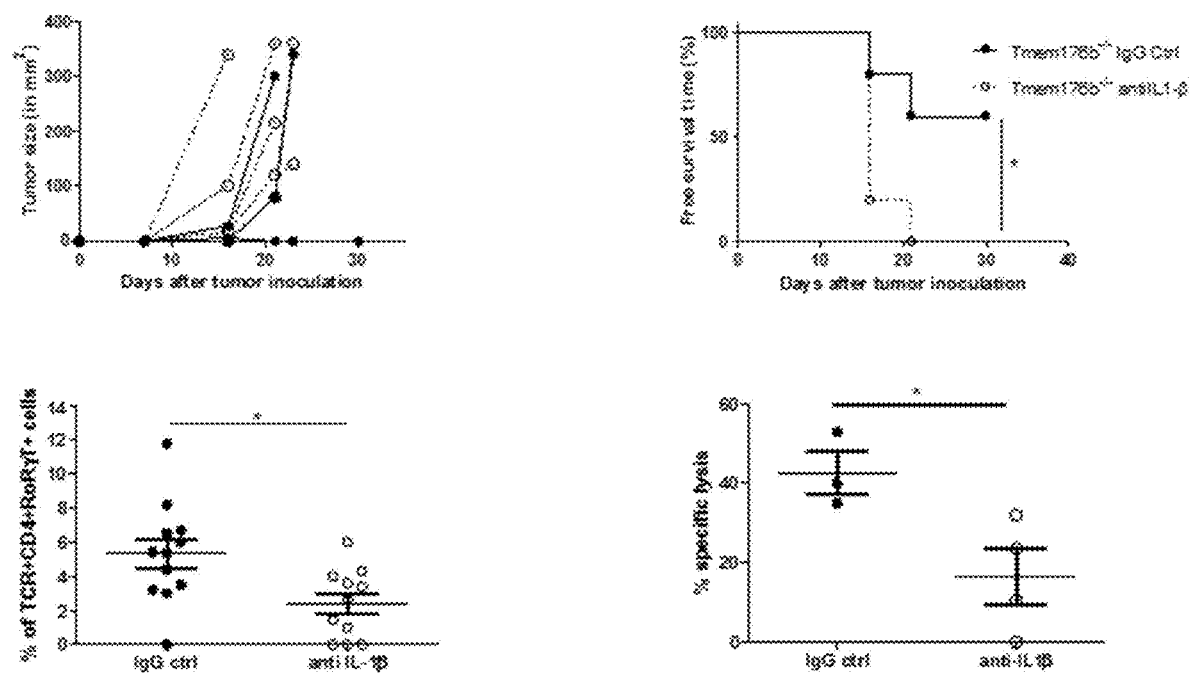
FIG. 7 shows the negative effect of in vivo IL-1 β blockade on CD8+ T cell specific anti-tumoral cytotoxicity and Th17 levels as well as on tumor free survival in TORID KO mice.

Without wishing to be bound by any theory, FIG. 6 illustrates a mechanism of regulating anti-tumoral CD8+ T cells via TORID manipulation. The initial steps required for creating downstream anti-tumoral CD8+ T cells includes IL-1β synthesis. Indeed, FIG. 6 and data presented herein demonstrate the importance of IL-1β synthesis in the progression toward generating anti-tumoral CD8+ T cells. FIG. 7 first shows the negative effect on CD8+ T cell-mediated in vivo cytotoxicity against tumoral antigens when IL-1β is blocked.

The study in FIG. 7 was performed by injecting 4 μg of control goat immunoglobulin (IgG Ctrl) or anti-IL-1β goat polyclonal antibodies into tumor bearing TORID KO mice by interperitoneal (i.p.) injection at 7 days, 12 days and 17 days after initial tumor cell injection. The data shows that tumor growth of the tumor bearing TORID KO mice treated with anti-IL-1β polyclonal antibodies was higher than the control group. Thus, neutralizing IL-1β in vivo leads to tumor growth. Moreover, the survival rate of the tumor bearing TORID KO mice treated with anti-IL-1β was significantly lower than the control group. The percentage of Tcrb, CD4, and RORγT cells was also markedly lower in the group treated with anti-IL-1β antibodies.

Indeed, the initial step of controlling IL-1β levels via TORID inhibition is an important factor for downstream anti-tumor effects. Thus, the inventors elucidated the association between TORID and IL-1β synthesis. As depicted in FIG. 6, IL-1β is dependent on inflammasome activation. For inflammasome-dependent IL-1β release, initial signals via toll-like receptor (TLR) stimulation increases pro-IL-1β synthesis. Thus, lipopolysaccharide (LPS) priming of BMDCs prior to stimulation lead to substantial increases in IL-1β production. Further, before IL-1β synthesis can occur, the NLRP3 inflammasome must be activated, which is influenced by caspase 1 activation. As shown in FIGS. 8 through 13, the association of TORID on these mechanisms that influence IL-1β levels is demonstrated.

Figure 8:
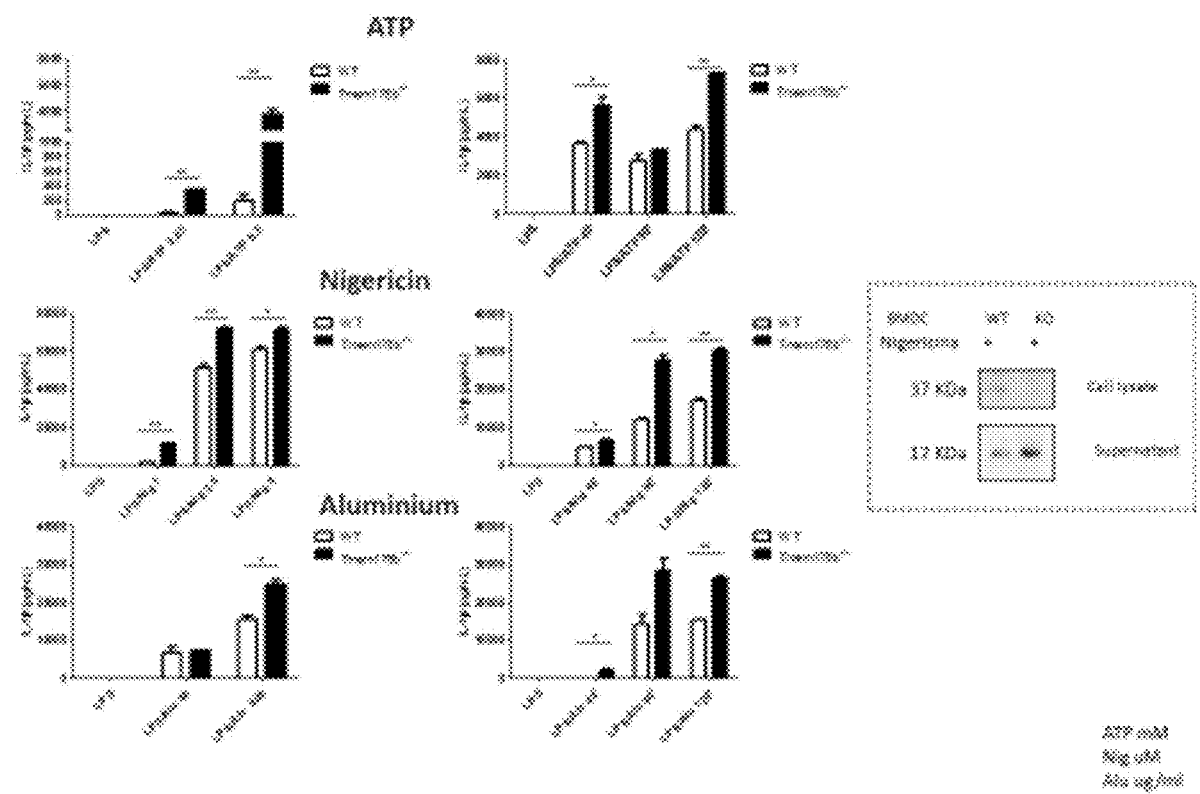
FIG. 8 shows that actively expressed Tmem176b inhibits inflammasome activation which in turn decreases IL-1β levels.

The study shown in FIG. 8 was performed by priming WT and TORID KO mice bone marrow-derived dendritic cells (BMDCs) with 0.25 μg/mL lipopolysaccharide (LPS) for four hours. The BMDCs were then washed and treated with different doses of ATP, Nigericin, and aluminum for 45 minutes as shown in the left column of bar graphs. Alternatively, 0.5 mg/mL ATP, 2.5 μg/mL Nigericin, or 500 μg/mL aluminum were used at different time points as indicated in the right column of bar graphs. IL-1β was quantified by ELISA in the culture supernatant. The western blot on the right demonstrates IL-1β of cell lysates and culture supernatant from wild type and TORID KO BMDCs. FIG. 8 shows that actively expressed Tmem176b inhibits inflammasome activation which in turn decreases IL-1β levels.

Figure 9:
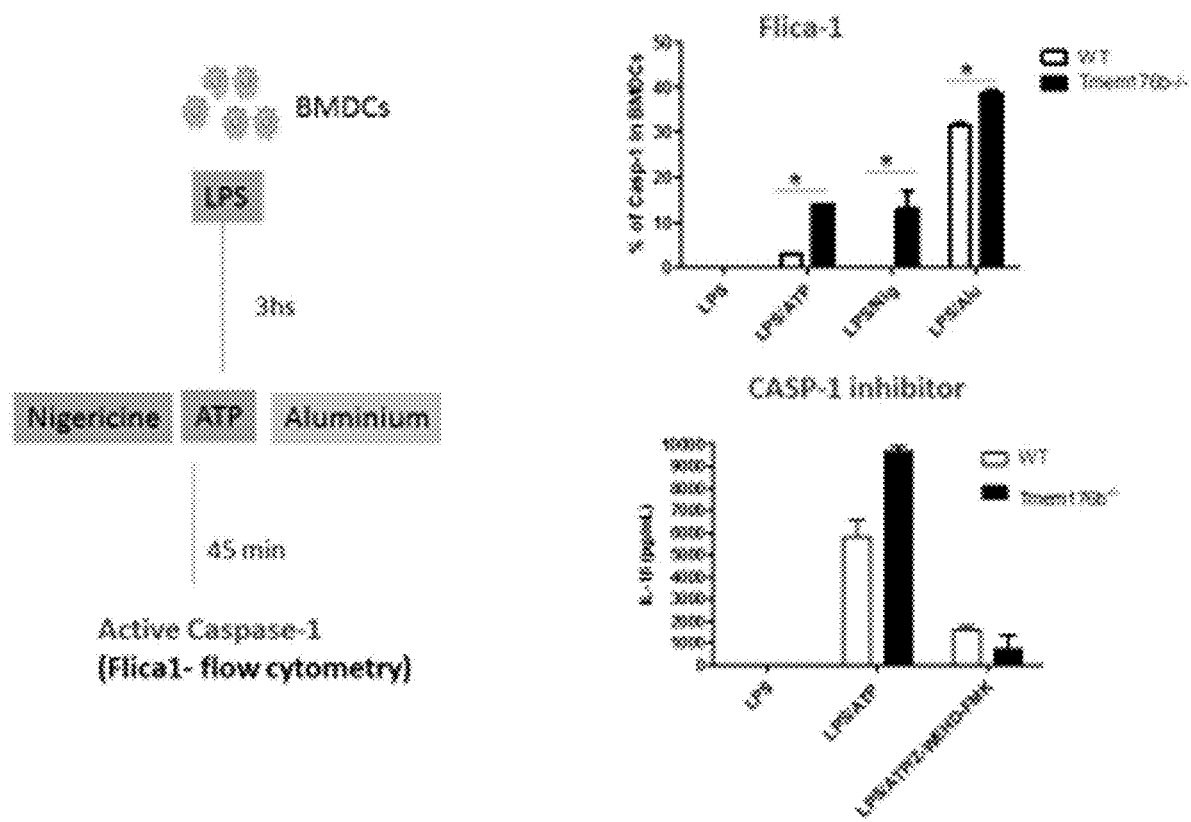
FIG. 9 demonstrates that inflammasome inhibition was controlled by specific impairment of caspase 1.
Figure 10:
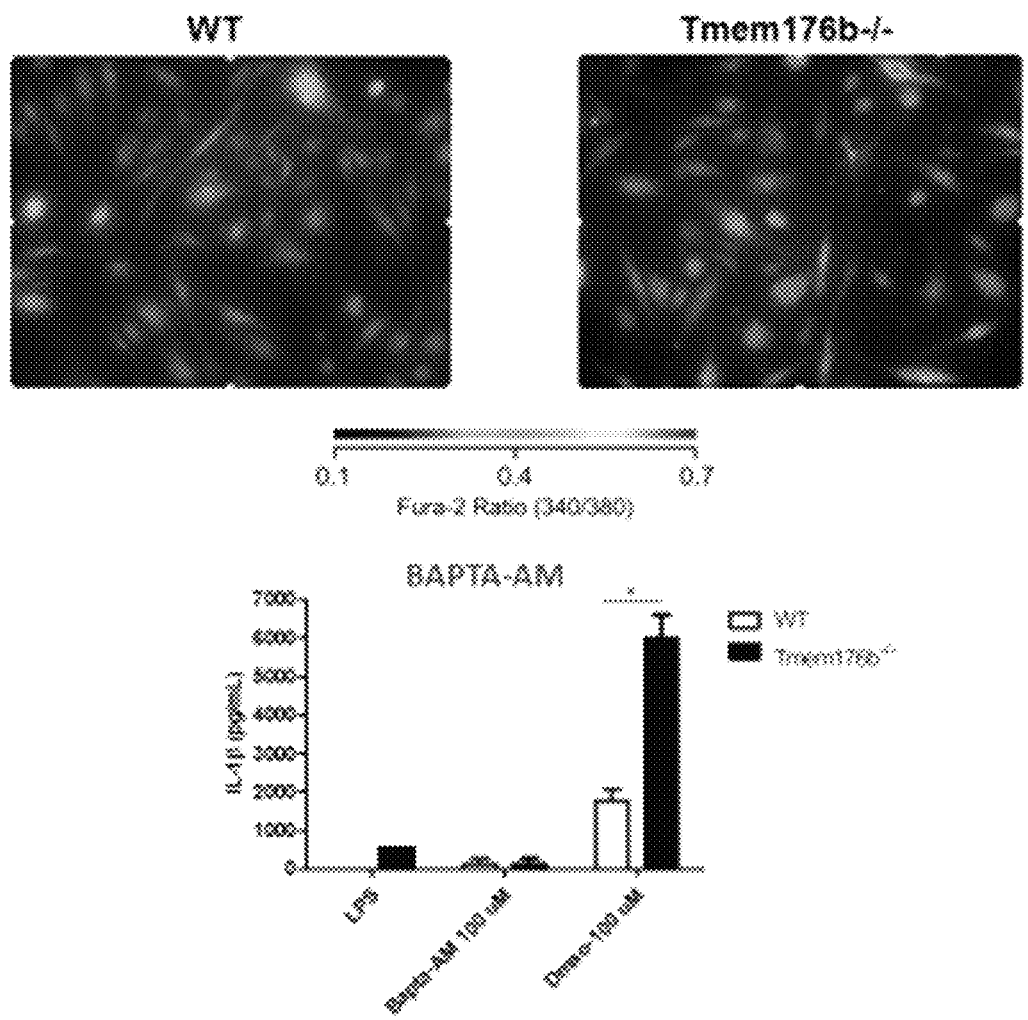
FIG. 10 shows that TORID KO BMDCs demonstrated higher cytosolic $Ca^{2+}$ levels than wild type mice when primed with LPS and stimulated with ATP.

FIG. 9 demonstrates that inflammasome inhibition was controlled by specific impairment of caspase 1. The experiment was performed on wildtype and TORID KO mice BMDCs primed with LPS for 3 hours. The BMDCs were subsequently treated with nigericin, ATP, or aluminum for 45 minutes. The upper right chart shows that caspase 1 activation is lower in all circumstances in wild type mice than in TORID KO mice. Caspase 1 activation was quantified by FACS using Flica 1 reagent. The lower right chart demonstrates that caspase 1 inhibition resulted in lower levels of IL-1β. Z-WEHD-FMK was used as the caspase 1 inhibitor, and IL-1β levels were quantified by ELISA in the supernatant of the cell culture stimulated with the indicated compounds.

Inflammasome activation is also associated with an increase of cytosolic $Ca^{2+}$. Thus, in another study shown in FIG. 10, TORID KO mice demonstrated higher cytosolic $Ca^{2+}$ levels than wild type mice. Data in this study was generated by loading $Ca^{2+}$ sensitive probe Fura-2 in wild type and TORID KO mice BMDCs after priming the BMDCs for three hours with LPS. The cells were exposed to 0.5 mM ATP to elicit inflammasome activation. The cells were excited with a UV laser at 350 nm. Absorbance at 340 nm and 380 nm were recorded in a time lapse manner. As shown in the top illustrations, the TORID KO BMDCs show a higher level of cytosolic $Ca^{2+}$. Moreover, IL-1β levels were higher with the TORID KO BMDCs. BAPTA-AM was used to chelate cytosolic $Ca^{2+}$. BAPTA-AM completely blocked IL-1β secretion in WT and TORID KO BMDC strongly suggesting that increased cytosolic $Ca^{2+}$ in TORID KO BMDCs leads to increased IL-1β secretion.

Figure 11:
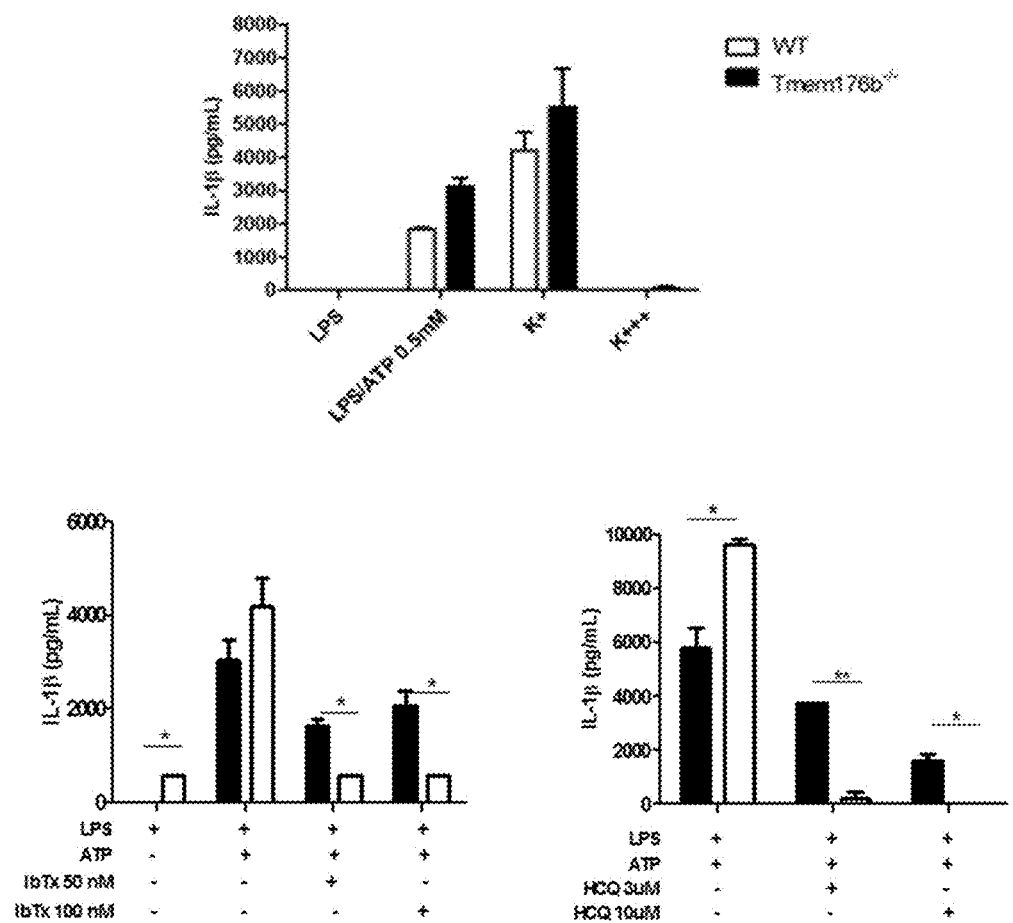
FIG. 11 demonstrates that $K^+$ efflux is needed by WT and TORID KO BMDCs to secrete IL-1β. $Ca^{++}$-activated $K^+$ channels inhibition by iberiotoxin (ibtx) or hydroxychloroquine (HCQ) controls IL-1β secretion by WT and TORID KO BMDCs.

Potassium ($K^+$) efflux is also linked to inflammasome activation. In the study shown in FIG. 11, IL-1β synthesis resulting from $K^+$ was tested. This study was performed on wild type and TORID KO mouse BMDCs treated with LPS and ATP as in the previously described studies herein. Culture medium was replaced by saline buffer containing normal low levels of $K^+$ (5 mM, K+) or high levels of $K^+$ (120 mM; K+++). IL-1β was quantified by ELISA in the culture supernatant. As shown in the top graph of FIG. 11, IL-1β levels were higher in the TORID KO mice. The absence of IL-1β secretion by WT and TORID KO BMDCs when the extracellular buffer contained high levels of $K^+$ strongly suggests that the efflux of this $K^+$ leads to inflammasome activation in both BMDCs. In agreement with these results, the bottom two graphs of FIG. 11 show that the inhibition of $Ca^2$-activated $K^+$ channels with the BKCa KCa1.1 specific inhibitor iberiotoxin blocked IL-1beta secretion n WT and TORID KO BMDCs. The antimalarial drogue hydroxychloroquine (HCQ) similarly inhibits inflammasome activation by inhibiting $Ca^{2+}$-activated $K^+$ channels KCa1.1 and KCa3.1. HCQ mimicked iberiotoxin in controlling IL-1β secretion in WT and TORID KO BMDCs. The results therefore support pharmacological use of TIs to promote inflammasome activation by triggering $Ca^{2+}$-activated $K^+$ channels.

Referring back to FIG. 6, synthesis of IL-1β leads to the promotion of anti-tumoral Th17 cells, which produce CD8+ T cells, as well as T cell receptors and tumor recognizing CD4+ T cells. CD4+ T cells generally orchestrate and regulate immune cells to provide immune surveillance against malignancy. Upon direct recognition of cancer cells, tumor-recognizing CD4+ T cells help CD8+ T cells by enhancing cytotoxic activity.

Figure 12:
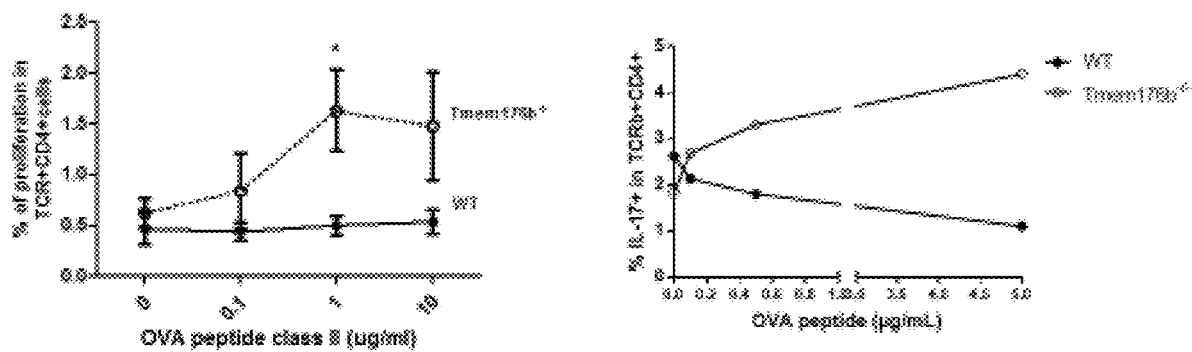
FIG. 12 presents data to support that $CD4^+$ T from TORID KO tumor-bearing mice proliferate significantly more and produce more IL-17 in vitro when re-stimulated with tumoral antigens (OVA).

FIG. 12 provides data to support that both CD4+ T cell and CD8+ T cell levels increase by inhibiting TORID. The tumor-draining lymph node (TDLN) of wild type and KO TORID tumor bearing—EG7.OVA cells—were analyzed twelve days after the tumor cell injection. A cell suspension was prepared, stained with the probe DDAO and cultured with the indicated doses of OVA class II peptide. Three days later, TCRb, CD4+ T cell proliferation was studied by FACS by analyzing DDAO dilution. In a similar experiment, intracellular IL-17 expression was studied by FACS in TCR and CD4 cells from the TDLN of wild type and KO TORID tumor bearing mice. As shown in FIG. 12, IL-17, TCRb, TCR and CD4+ T cell proliferation were found at higher levels than in the KO TORID mice than in the wild type mice.

Figure 13:
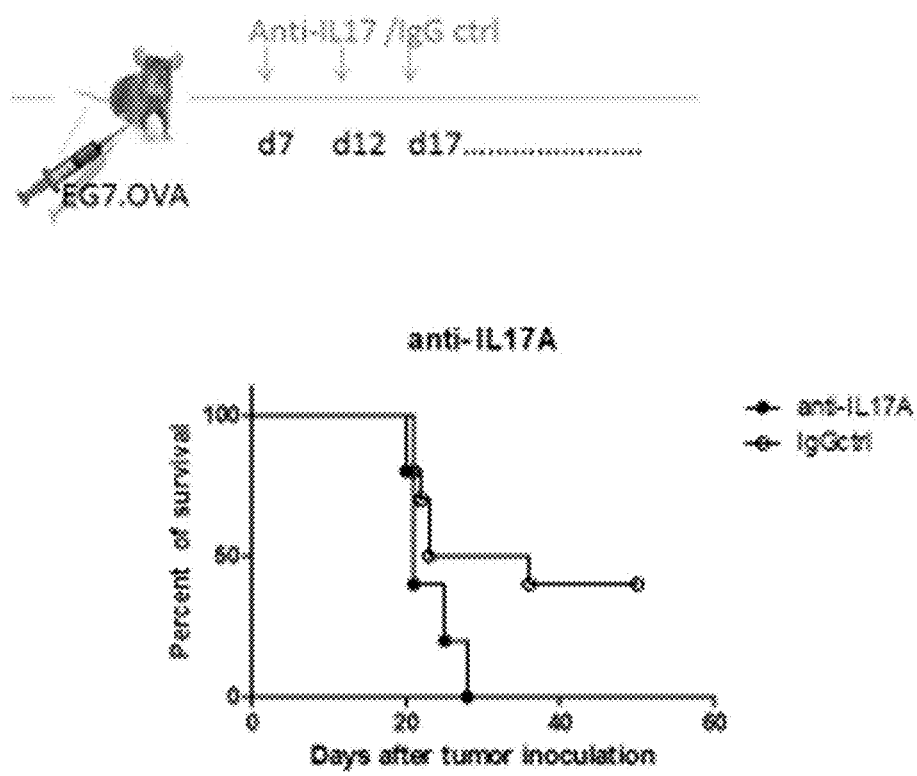
FIG. 13 demonstrated that neutralizing IL-17 diminished the rate of survival in mouse models.

In a complementary study, FIG. 13 demonstrated that neutralizing IL-17 diminished the rate of survival in mouse models. The study shown in FIG. 13 was performed by intraperitoneal (i.p.) injection of 4 μg of control goat immunoglobulin (IgG Ctrl) or anti-IL-17 goat polyclonal antibodies into wild type or KO TORID mice inoculated with EG7.OVA tumor cells. The i.p. injections of the IgG Ctrl or anti-IL goat polyclonal antibodies were given at 7, 12 and 17 days after inoculation of the EG7.OVA tumor cells. Survival times of the two groups are shown in FIG. 13. The data indicates that neutralizing IL-17 with anti-IL-17 antibodies lead to diminished rates of survival.

From FIGS. 1-13, the inventors established the association of TORID with anti-tumor CD8+ T cell generation, and ultimately the association of TORID and tumor cell regulation. The inventors further discovered that anti-tumor CD8+ T cell generation and tumor regulation of TORID inhibited pharmacologically by an ion-channel ligands is a phenocopy of the TORID KO results. Preferably, the pharmacological agent is a TORID Inhibitor (TI). More preferably, the TI is BAY K8644.

Figure 14:
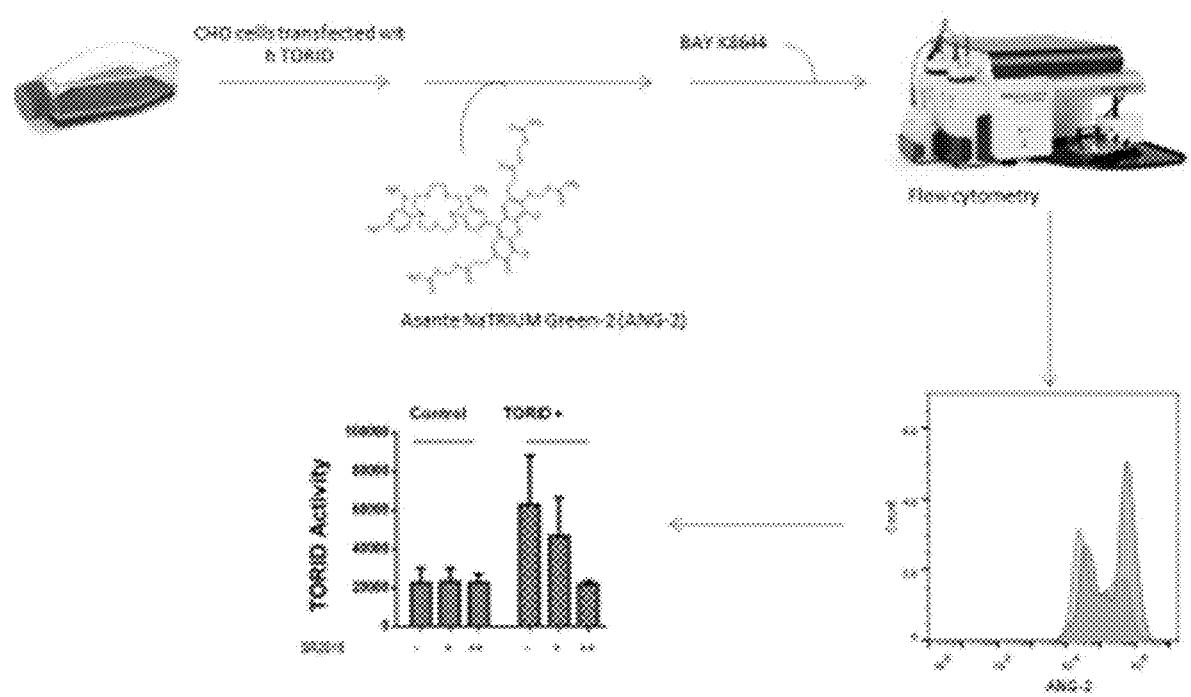
FIG. 14 FACS analysis indicates that BAY K8644 inhibits TORID activity.
Figure 15:
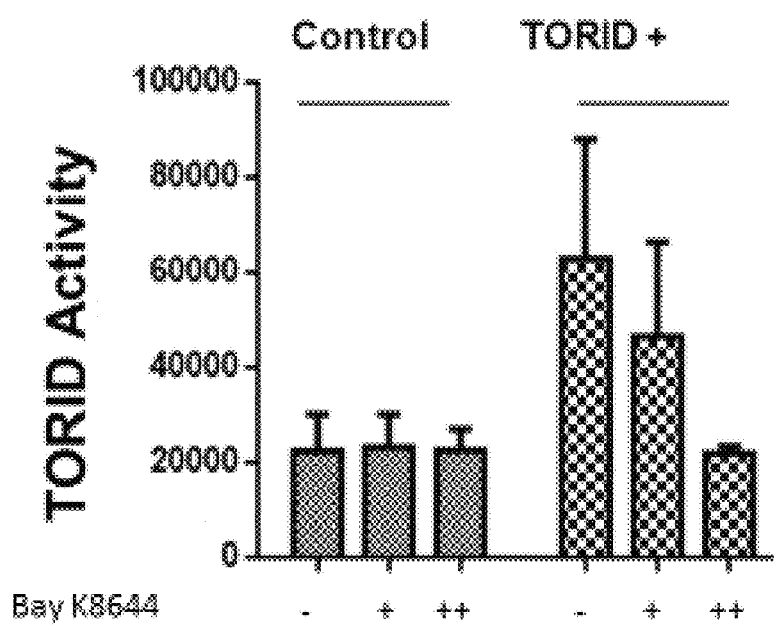
FIG. 15 illustrates analysis of the ANG-2 mean fluorescent intensity (MFI) in normal medium of TORID exposed to BAY K8644 concentrations of 0 uM (−), 5 uM (+) or 10 uM (++).

As shown in FIG. 14 Chinese hamster ovarian (CHO) cells were transfected with TORID and Tmem176a and incubated for 24 hours. The cells were subsequently loaded with ANG-2 probe for 30 min RT, washed, and then incubated with (+)-BAY K8644 or (i)-BAY K8644 for 30 min. The cells were then analyzed by flow cytometry to evaluate TORID activity. Activity was measured by comparing fluorescence of the ANG-2 probe in TORID+ cells incubated with BAY K8644 (blue) to the control (red). TORID activity measure as the ANG-2 mean fluorescent intensity (MFI) in normal medium 0(−), 5(+), or 10(++) uM. The change in fluorescent intensity shown in FIG. 14 indicates that BAY K8644 inhibits TORID activity. FIG. 15 illustrates analysis of the ANG-2 mean fluorescent intensity (MFI) in normal medium of TORID exposed to BAY K8644 concentrations of 0 uM (−), 5 uM (+) or 10 uM (++). Diminishing TORID activity starting from 0 uM (−) to 10 um (++) of BAY K8644 demonstrates a dose proportional response to BAY K8644. In all cases fluorescence intensity from ANG-2-loaded cells cultured in Natfree buffer was subtracted.

Figure 16:
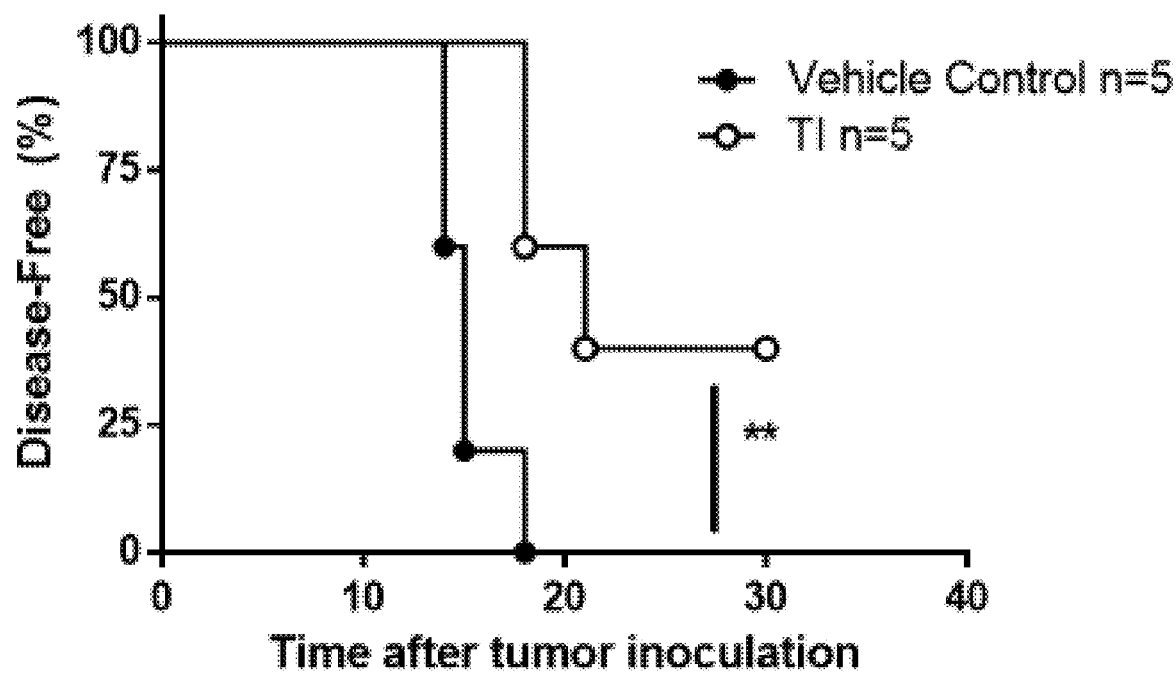
FIG. 16 confirm the effect of pharmacologic inhibition of TORID on tumor growth.

Data from in vivo studies depicted in FIG. 16 confirm the effect of pharmacologic inhibition of TORID on tumor growth. The study was performed on wild type mice injected subcutaneously with EG7.OVA cancer cells. Three days after inoculating the wild type mice with EG7.OVA tumor cells, Bay K8644 or a control vehicle, such as ethanol, were injected intraperitoneally daily up to the fifteenth day after tumor cell inoculation. As shown in FIG. 16, disease-free survival rates of tumor bearing wild type mice injected with BAY K8644 increased thereby illustrating that pharmacologic inhibition of TORID—preferably BAY K8644—are therapeutic candidates for cancer treatment.

Figure 17:
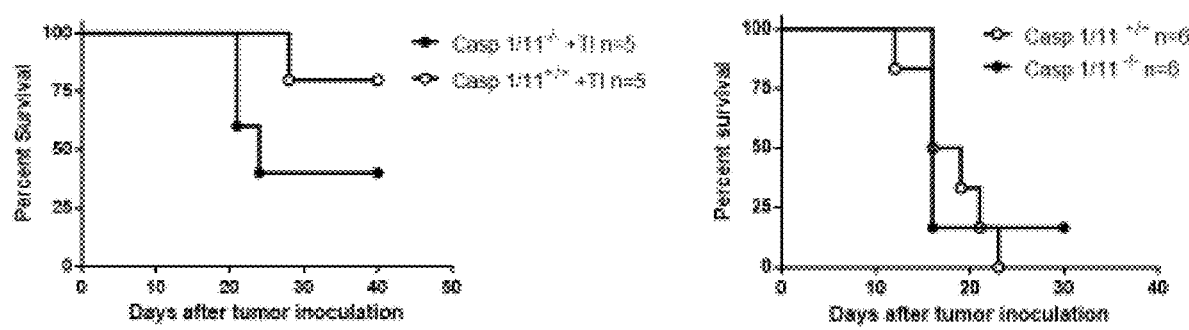
FIG. 17 presents data indicating that the absence of caspase 1 activity (i.e. $1/11^{-/-}$) lowered the survival rate of tumor bearing mice, and that overall rates of survival in tumor bearing mice that were injected with BAY K8644 was higher.

FIG. 17 further confirms the results from FIG. 16 and the proposed mechanism depicted in FIG. 6. Data shown in FIG. 17 was gathered from caspase 1/11 active mice ($1/11^{+/+}$) and caspase 1/11 KO mice ($1/11^{-/-}$) injected with EG7.OVA cells. The chart on the left shows the results from the mice intraperitoneally injected with 4 mg/kg of BAY K8644 daily starting from the third day after inoculation of tumor cells up to the fifteenth day after inoculation of tumor cells. The data shows that the absence of caspase 1 activity (i.e. $1/11^{-/-}$) lowered the survival rate of tumor bearing mice.

The chart on the right, in FIG. 17, shows the results of the negative control group, which was not injected with BAY K8644. A comparison shows that overall rates of survival in tumor bearing mice that were injected with BAY K8644 was higher.

Figure 18:
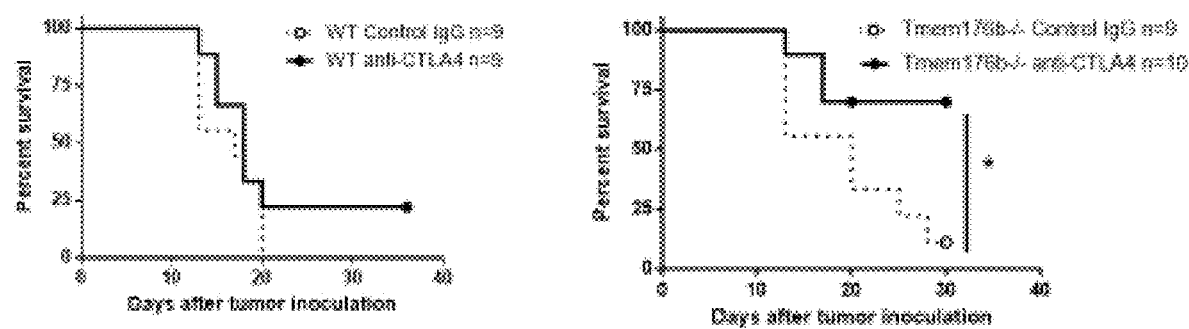
FIG. 18 shows the effect of anti-CTLA4 therapy between wild type and TORID KO mice.
Figure 19:
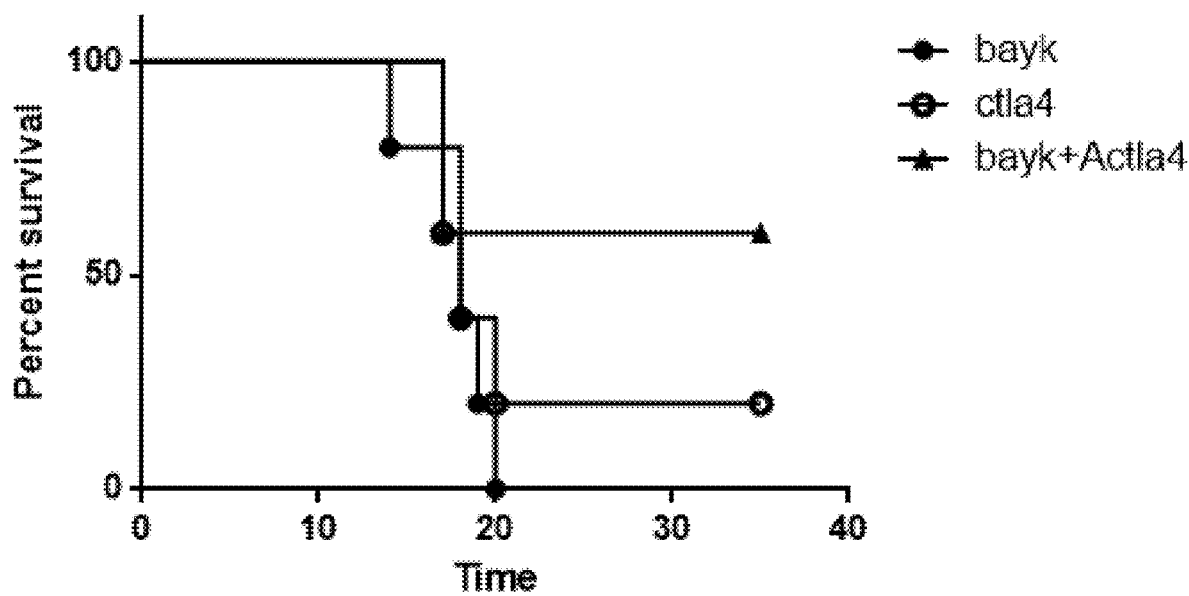
FIG. 19 shows that BAY K8644 and anti-CTLA-4 antibody co-treatment improved percent survival in comparison to mono-treatment with BAY K8644 or anti-CTLA-4 antibody alone.

FIG. 18 shows the effect of anti-CTLA4 therapy between wild type and TORID KO mice. The data provides support for viable tumor treatment with a combination of pharmacologic TORID inhibition—preferably by BAY K8644—in combination with anti-CTLA4 treatment. The data shown in the left chart in FIG. 18 was gathered from wild type mice injected subcutaneously with EG7.OVA cancer cells, whereas the chart on the right represents results from TORID KO mice injected with the same. In both cases, the mice were injected with either control IgG or with anti-CTLA4 antibodies. The antibodies were injected at 100 amounts at 4, 7, 11, and 15 days after tumor inoculation. The survival rates show that overall all TORID KO mice had a higher rate of survival. Moreover, the chart on the right showed that TORID KO mice receiving anti-CTLA4 treatment had the highest rates of survival. FIG. 19 demonstrates results from WT mice injected with EG.7 cells and then treated with BAY K8644 (1 mg/kg for 12 days (days 3-15), anti-CTLA4 (100 μg/injection, 4 injections at days (+7, +10 and +13) or both treatments. As shown in the graph, BAY K8644 and anti-CTLA-4 antibody co-treatment improved percent survival in comparison to mono-treatment with BAY K8644 or anti-CTLA-4 antibody alone.

Administration

Therapeutic agents within the scope of the present invention can be administered by one or more ways. For example, the following routes may be utilized: oral, parenteral (including subcutaneous injections, intravenous, intramuscular, intrasternal injection or infusion techniques), inhalation, buccal, sublingual, or rectal, in the form of a unit dosage of a pharmaceutical composition containing an effective amount of the compound and optionally in combination with one or more pharmaceutically-acceptable excipients such as stabilizers, anti-oxidants, lubricants, bulking agents, fillers, carriers, adjuvants, vehicles, diluents and other readily known excipients in standard pharmaceutical practice.

Liquid preparations suitable for oral administration (e.g. suspensions, syrups, elixirs and other similar liquids) can employ media such as water, glycols, oils, alcohols, and the like. Solid preparations suitable for oral administration (e.g. powders, pills, capsules and tablets) can employ solid excipients such as starches, sugars, kaolin, lubricants, binders, disintegrating agents, antioxidants and the like.

Parenteral compositions typically employ sterile water as a carrier and optionally other ingredients, such as solubility aids. Injectable solutions can be prepared, for example, using a carrier comprising a saline solution, a glucose solution or a solution containing a mixture of saline and glucose. Further guidance for methods suitable for use in preparing pharmaceutical compositions is provided in Remington: The Science and Practice of Pharmacy, $21^{st}$ edition (Lippincott Williams & Wilkins, 2006).

In another embodiment the active agent prepared as described above which are formulated as a solid dosage form for oral administration including capsules, tablets, pills, powders, and granules. In such embodiments, the active compound may be admixed with one or more inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents and can additionally be prepared with enteric coatings. The means and methods for tableting are known in the art and one of ordinary skill in the art can refer to various references for guidance. For example, *Pharmaceutical Manufacturing Handbook: Production and Processes*, Shayne Cox Gad, John Wiley & Sons, Inc., Hoboken, N.J. (2008), which is hereby incorporated by reference in its entirety can be consulted.

The active agent can be administered orally in a dosage range of about 0.001 to 1000 mg/kg of mammal (e.g. human) body weight per day in a single dose or in divided doses. One dosage range is about 0.01 to 500 mg/kg body weight per day orally in a single dose or in divided doses. For oral administration, the compositions can be provided in the form of tablets or capsules containing about 1.0 to 500 mg of the active ingredient, particularly about 1, 5, 10, 15, 20, 25, 50, 75, 100, 150, 200, 250, 300, 400, 500, and 750 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. In view of the factors affecting the specific dose level and frequency it is contemplated that the dose frequency can range from multiple doses daily to monthly dosages. The preferred dose frequency ranges from twice a day to every two weeks. A more preferred dose frequency ranges from twice a day to weekly. A most preferred dose frequency ranges from twice a day to twice a week.

The following general methods are used in order to describe and demonstrate biological activity and potential therapy usage of compounds of the present invention only, and are not to be construed in any way as limiting the scope of the invention.

Immune Checkpoint Blockade (ICB) Treatment with BAY K8644

Another embodiment of the current invention includes a method of treating cancer patients resistant to anti-PD-1 therapy with BAY K8644.

Without wishing to be bound by theory, a therapeutically effective amount of BAY K8644 may be used to treat cancer in patients with inflammasome-related genes associated with clinical responses in ICB-treatment. Specifically, cancer patients showing resistance to anti-PD-1 therapy are expected to benefit from a therapeutically effective amount of BAY K8644 treatment due to the inhibitory effects on TORID, which would stimulate up-regulation of inflammasome activation.

Figure 20:
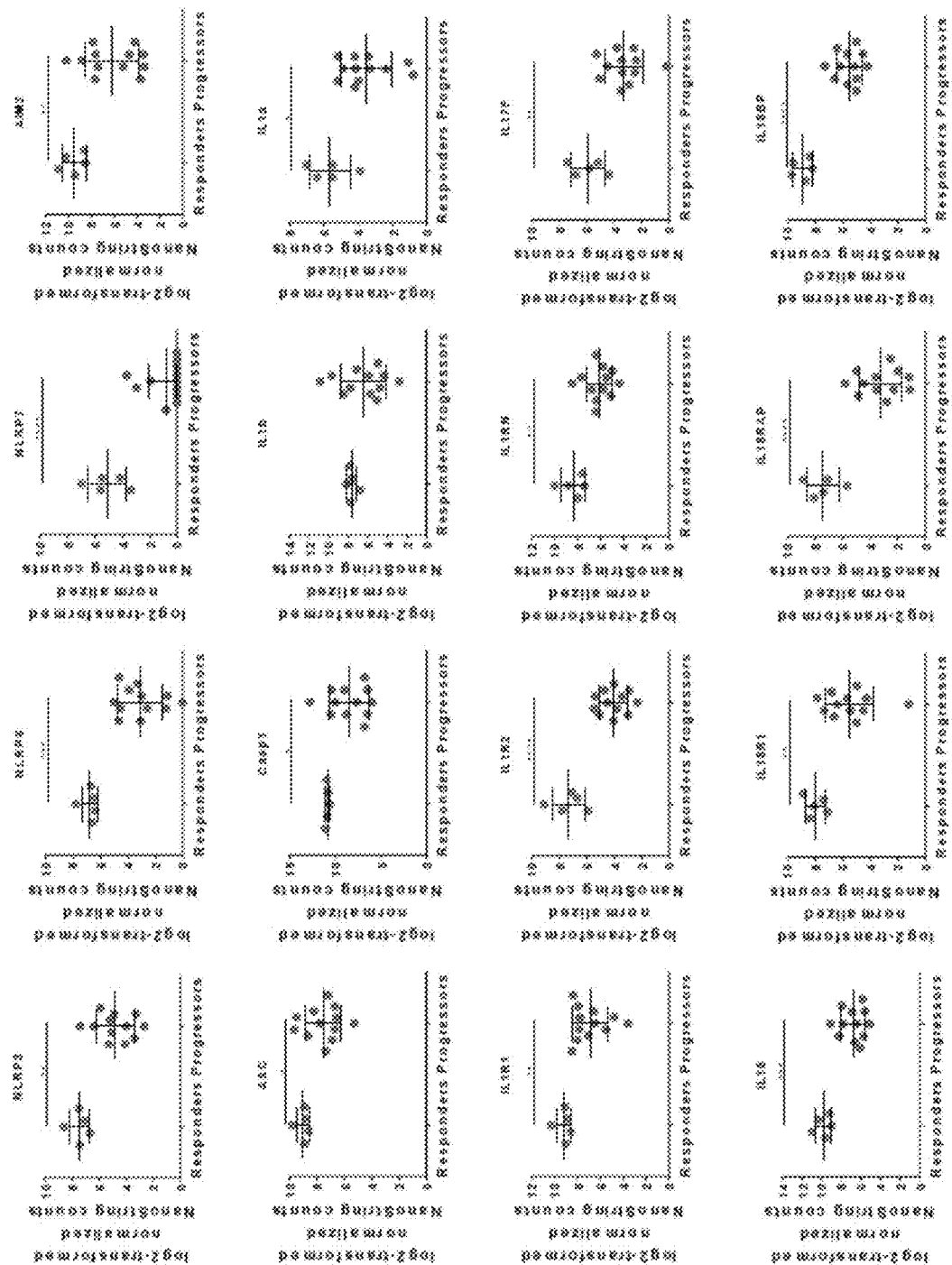
FIG. 20 shows the expression of 16 inflammasome-related genes in tumor biopsies from responding and progressing melanoma patients being treated with anti-PD1 antibody.
Figure 21:
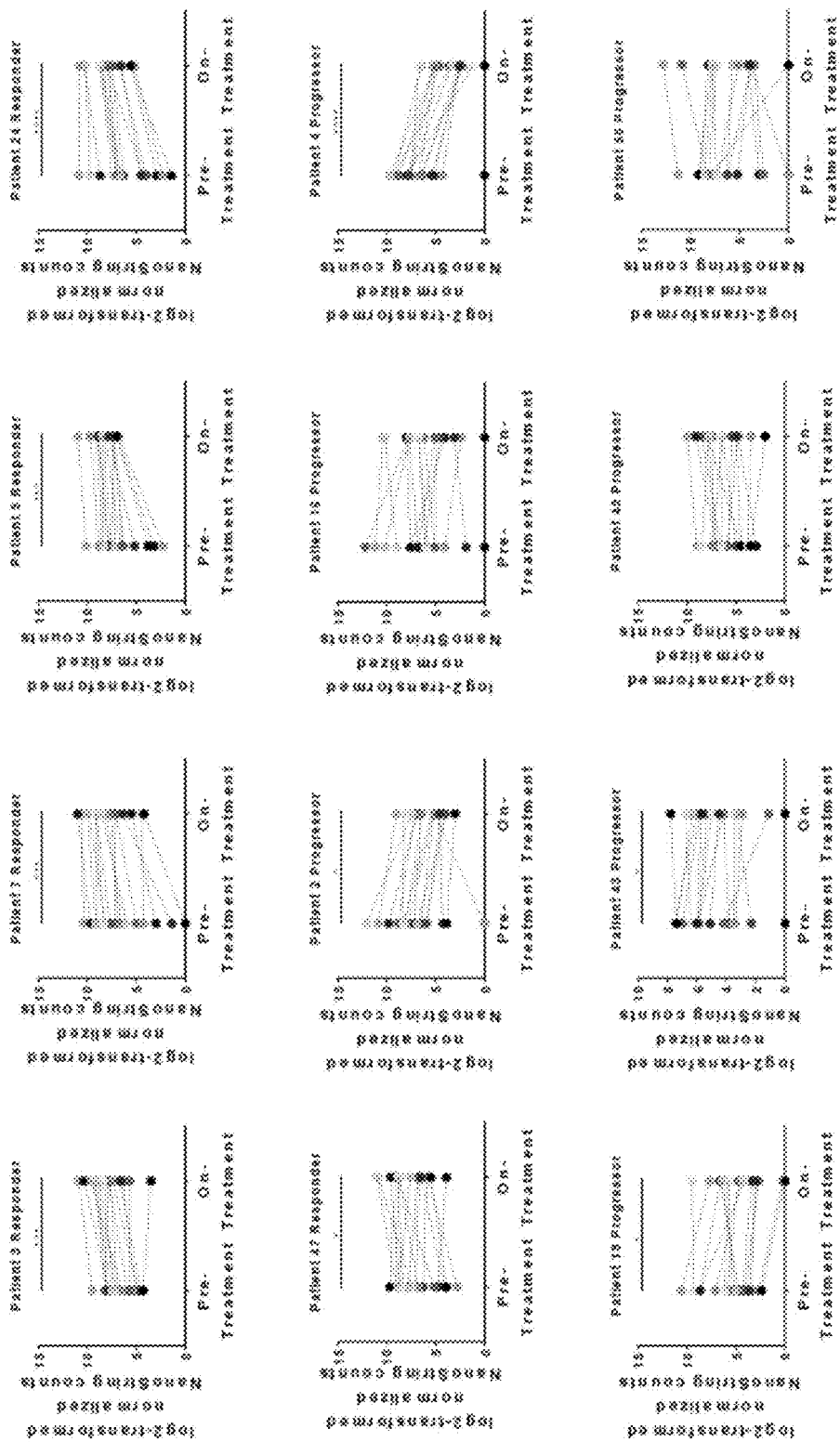
FIG. 21 presents a paired analysis of the expression of 16 inflammasome-related genes in tumor biopsies from five responding and seven progressive melanoma patients comparing expression before and during anti-PD-1 treatment.

As described in further detail, the expression of the inflammasome indicates promotion of ICB-triggered tumor immunity. For example, the gene expression profiling (GEP) of responders versus progressive patients were not significantly different when tested before anti-CTLA-4 treatment, after anti-CTLA-4 treatment, and before anti-PD-1 treatment. However, after anti-PD-1 treatment, 15 of 16 inflammasome-related genes were significantly upregulated in responders as compared to progressive patients as shown in FIG. 20. FIG. 21 further supports that inflammasome-related genes are associated with clinical responses in ICB-treated patients by showing that 5 of 5 patients responding to anti-PD-1 showed a significant up-regulation of inflammasome-related genes during anti-PD-1 treatment. Moreover, 4 of 7 patients who did not respond to anti-PD-1 treatment demonstrated significant downregulation of the inflammasome signature as shown in FIG. 21. These results indicate that inflammasome activation promotes ICB-triggered tumor immunity.

Figure 22:
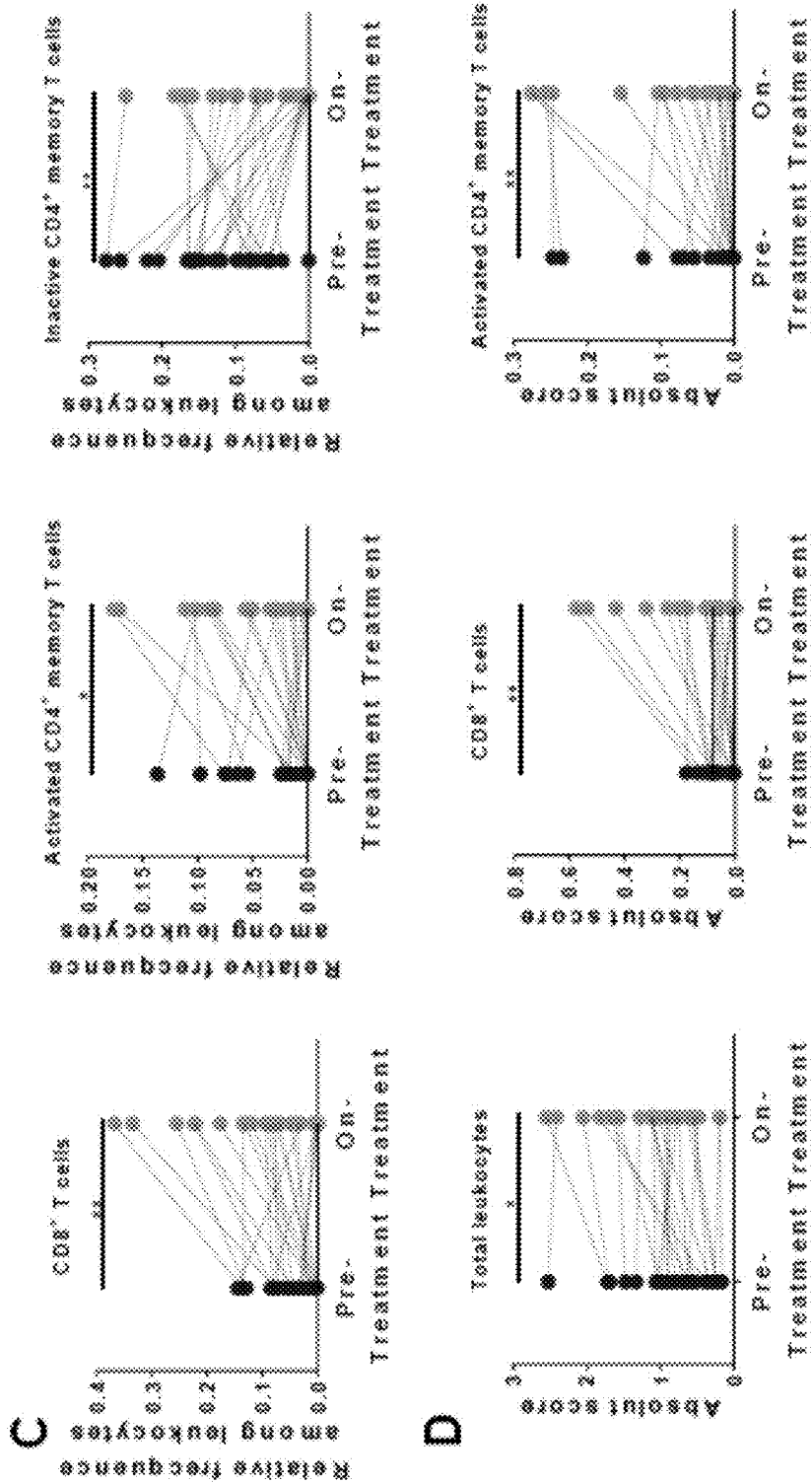
FIG. 22 Presents a CIBERSORT analysis quantifying the depicted cell populations within tumor biopsies from responding melanoma patients to anti-PD-1 therapy.
Figure 23:
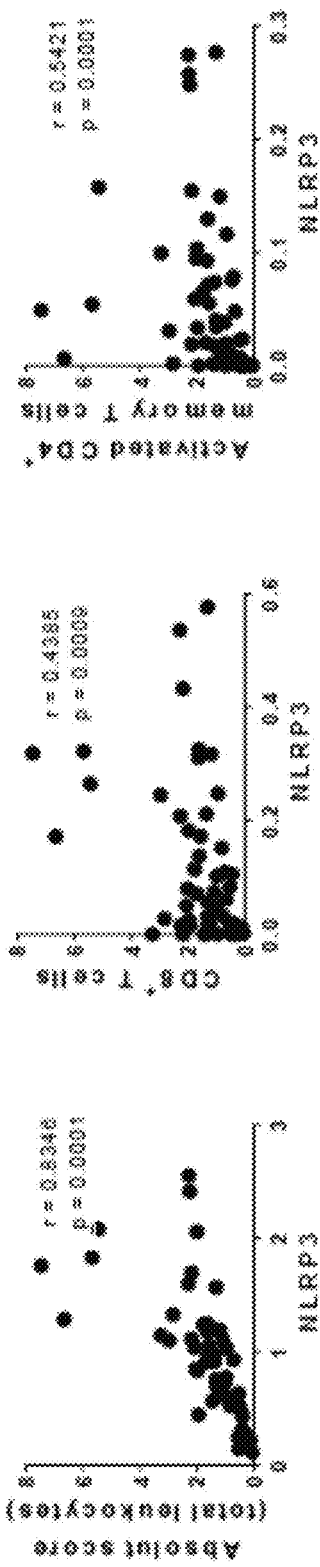
FIG. 23 shows correlation analysis of the indicated leukocyte populations infiltrating human melanoma tumors (responding to anti-PD-1) with tumoral NLRP3 expression.

Further analysis of leukocyte populations infiltrating the tumor through the CIBERSORT method provided similar conclusions. As shown in FIG. 22A, responding patients showed increased relative frequencies of $CD8^+$ T cells and activated memory $CD4^+$ T cells during anti-PD-1 therapy compared to diminished inactive memory $CD4^+$ T cells during the pre-treatment stage. Progressive patients showed no such response. FIG. 22B also shows that responding patients demonstrated an elevated absolute total number of leukocytes, $CD8^+$ T cells and activated memory $CD4^+$ T cells. FIG. 23 demonstrates that the total number of leukocytes as well as the frequency of $CD8^+$ T cells and activated memory $CD4^+$ T cells were significantly associated with expression of inflammasome (NLRP3) expression.

Figure 24:
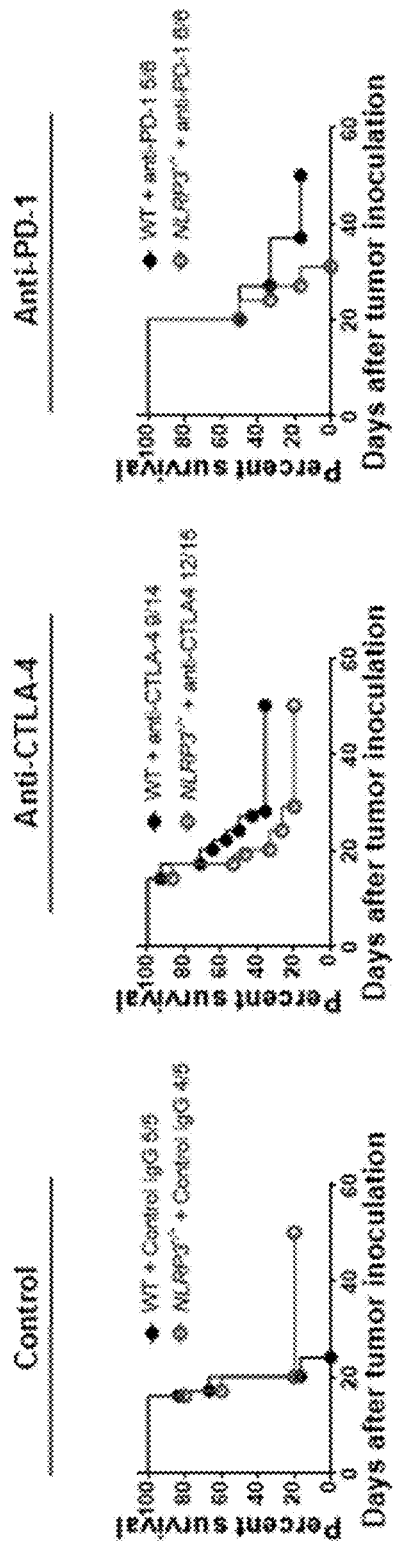
FIG. 24 demonstrates the survival analysis of the indicated groups of animals and treatments. The ratio depicts the number of cancer-dying animals/total injected mice. As shown, NLRP3 knock-out mice showed a great decrease in survival even with anti-PD-1 therapy.
Figure 25:
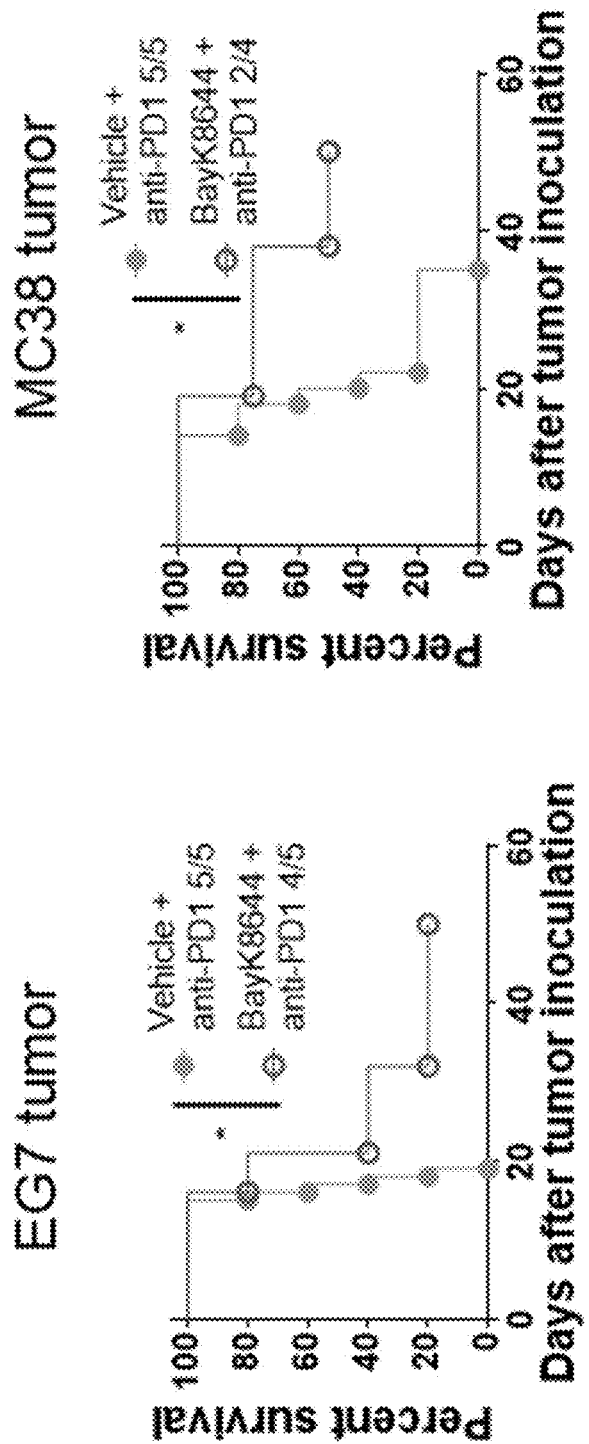
FIG. 25 shows the survival analysis of the indicated groups of mice injected with EG7 and MC38 tumors and treated with anti-PD-1 alone or anti-PD-1+Bayk8644.

FIGS. 24 and 25 demonstrate that administering BAY K8644 to control TORID and downstream inflammasome expression increases survival in mice that may show resistance to anti-PD-1 therapy. For example, FIG. 24 shows that wild type mice responded to anti-PD-1 therapy and had an increased survival rate, whereas, NLRP3 knock-out mice showed a noticeable decrease in survival, which corresponds to the conclusions drawn from studies illustrated in FIGS. 20-23. FIG. 25 demonstrates that administering BAY K8644 inhibits TORID activity and elicits increased inflammasome (NLRP3) expression, which results in a higher rate of survival in two tumor types in anti-PD-1 resistant mice.

These observations reinforce that BAY K8644 inhibition of TORID to increase inflammasome activation provides a benefit to patients that are resistant to anti-PD-1 therapy. Thus, another embodiment within the scope of the present invention includes a method of treating anti-PD-1 resistant cancer patients, which includes the steps of performing a pre-treatment biopsy of a patient, administering anti-PD-1 treatment to the patient, evaluating inflammasome-related gene expression, performing a post-treatment biopsy, comparing pre-treatment and post-treatment biopsies; and if inflammasome-related gene expression is low and/or down-regulated post-treatment as compared to pre-treatment then administering the patient with a therapeutically effective amount of BAY K8644.

NON-PATENT CITATIONS

1. Sharma, P. and J. P. Allison, "Immune checkpoint targeting in cancer therapy: toward combination strategies with curative potential." *Cell* 161(2): 205-214 (2015).
2. Topalian, S. L., C. G. Drake and D. M. Pardoll, "Immune checkpoint blockade: a common denominator approach to cancer therapy." *Cancer Cell* 27(4): 450-461 (2015).
3. Baumeister, S. H., G. J. Freeman, G. Dranoff and A. H. Sharpe, "Coinhibitory Pathways in Immunotherapy for Cancer." *Annu Rev Immunol* 34: 539-573 (2016).
4. Twyman-Saint Victor, C., A. J. Rech, A. Maity, R. Rengan, K. E. Pauken, E. Stelekati, J. L. Benci, B. Xu, H. Dada, P. M. Odorizzi, R. S. Herati, K. D. Mansfield, D. Patsch, R. K. Amaravadi, L. M. Schuchter, H. Ishwaran, R. Mick, D. A. Pryma, X. Xu, M. D. Feldman, T. C. Gangadhar, S. M. Hahn, E. J. Wherry, R. H. Vonderheide and A. J. Minn, "Radiation and dual checkpoint blockade activate non-redundant immune mechanisms in cancer." *Nature* 520(7547): 373-377 (2015).
5. Louvet, C., E. Chiffoleau, M. Heslan, L. Tesson, J. M. Heslan, R. Brion, G. Beriou, C. Guillonneau, J. Khalife, I. Anegon and M. C. Cuturi, "Identification of a new member of the CD20/FcepsilonRIbeta family overexpressed in tolerated allografts." *Am J Transplant* 5(9): 2143-2153 (2005).

6. Condamine, T., L. Le Texier, D. Howie, A. Lavault, M. Hill, F. Halary, S. Cobbold, H. Waldmann, M. C. Cuturi and E. Chiffoleau, "Tmem176B and Tmem176A are associated with the immature state of dendritic cells." *J Leukoc Biol* 88(3): 507-515 (2010).
7. Segovia, M., C. Louvet, P. Charnet, A. Savina, G. Tilly, L. Gautreau, L. Carretero-Iglesia, G. Beriou, I. Cebrian, T. Cens, L. Hepburn, E. Chiffoleau, R. A. Floto, I. Anegon, S. Amigorena, M. Hill and M. C. Cuturi, "Autologous dendritic cells prolong allograft survival through Tmem176b-dependent antigen cross-presentation."*Am J Transplant* 14(5): 1021-1031 (2014).
8. Nishikawa, H and Sakaguchi, S., "Regulatory T cells in tumor immunity." Int. J. Cancer 127: 759-767 (2010).

What is claimed is:

1. A method of impairing tumor growth in a mammal having a tumor resistant to anti-PD-1 therapy, anti-CTLA4 therapy, or a combination thereof, comprising administering to the mammal, a pharmaceutical composition comprising (+)-BAY K8644 and at least one pharmaceutically acceptable excipient.

2. The method of claim 1, further comprising administering one or more second therapeutic agents to the mammal.

3. The method of claim 2, wherein the second therapeutic agent is an anti-CTLA4 antibody or an anti-PD-1/PD-L1 antibody.

4. The method of claim 2, wherein the second therapeutic agent is radiation therapy.

5. The method of claim 3, further comprising administering radiation therapy to the mammal.

6. The method of claim 1, wherein the tumor is melanoma.

7. A method of impairing tumor growth in a mammal having a tumor resistant to anti-PD-1 therapy, anti-CTLA4 therapy, or a combination thereof, comprising administering to the mammal, a pharmaceutical composition comprising from about 0.01 mg/kg to about 500 mg/kg of (+)-BAY K8644 and at least one pharmaceutically acceptable excipient.

8. The method of claim 7, wherein the amount of (+)-BAY K8644 is from 1 mg/kg to 4 mg/kg.

9. The method of claim 8, wherein the tumor is melanoma.

10. The method of claim 7, wherein (+)-BAY K8644 is administered with at least one secondary agent.

11. The method of claim 10, wherein the second therapeutic agent is radiation therapy.

12. The method of claim 11, wherein the tumor is melanoma.

13. The method of claim 10, wherein the second therapeutic agent is anti-CTLA4 antibody or anti-PD-1/PD-L1 antibody.

14. The method of claim 13, further comprising administering radiation therapy to the mammal.

15. The method of claim 14, wherein the tumor is melanoma.

* * * * *